(12) United States Patent
Bottlang et al.

(10) Patent No.: US 10,918,430 B2
(45) Date of Patent: *Feb. 16, 2021

(54) BONE SCREW WITH MULTIPLE THREAD PROFILES FOR FAR CORTICAL LOCKING AND FLEXIBLE ENGAGEMENT TO A BONE

(71) Applicant: Zimmer, Inc., Warsaw, IN (US)

(72) Inventors: Michael Bottlang, Happy Valley, OR (US); Michael K. Keith, Winona Lake, IN (US); Josef Doornink, Portland, OR (US); Anthony Lee Koser, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/097,939

(22) Filed: Apr. 13, 2016

(65) Prior Publication Data

US 2016/0220290 A1 Aug. 4, 2016

Related U.S. Application Data

(63) Continuation of application No. 14/265,662, filed on Apr. 30, 2014, now Pat. No. 9,314,286, which is a
(Continued)

(51) Int. Cl.
*A61B 17/86* (2006.01)
*A61B 17/80* (2006.01)
*A61B 17/16* (2006.01)

(52) U.S. Cl.
CPC ............ *A61B 17/863* (2013.01); *A61B 17/80* (2013.01); *A61B 17/8042* (2013.01); *A61B 17/16* (2013.01); *A61B 17/8057* (2013.01)

(58) Field of Classification Search
CPC .... F16B 35/041; F16B 35/048; A61B 17/863; A61B 17/16; A61B 17/8042; A61B 17/8057; A61B 17/7059; A61B 17/70
(Continued)

(56) References Cited

U.S. PATENT DOCUMENTS 2,060,593 A * 11/1936 Schaurte ................. F16B 31/06
470/11
4,125,050 A * 11/1978 Schwartzman ..... F16B 25/0084
408/228
(Continued)

FOREIGN PATENT DOCUMENTS

JP 2009527279 A 7/2009
JP 2010517673 A 5/2010
(Continued)

OTHER PUBLICATIONS

U.S. Appl. No. 11/058,935, filed Feb. 15, 2005, Bone Screw for Positive Locker but Flexible Engagement to a Bone.
(Continued)

*Primary Examiner* — Ellen C Hammond
*Assistant Examiner* — Tara Rose E Carter
(74) *Attorney, Agent, or Firm* — Schwegman Lundberg & Woessner, P.A.

(57) ABSTRACT

Osteosynthesis constructs for treating bone fractures and bone screws for use in such systems are disclosed. The bone screws include a threaded front section configured for engagement with cortical bone, a threaded mid-section and an unthreaded neck section configured for limited movement within the near cortex of the bone. Osteosynthesis constructs of the type disclosed promote secondary healing by allowing for substantially parallel motion at the near and far cortex within the effective motion range for callus formation.

19 Claims, 7 Drawing Sheets

Related U.S. Application Data continuation of application No. 13/040,066, filed on Mar. 3, 2011, now Pat. No. 8,740,955, which is a continuation-in-part of application No. 11/058,935, filed on Feb. 15, 2005, now Pat. No. 8,197,523.

(58) Field of Classification Search
USPC .......................... 606/300–320; 411/411, 424
See application file for complete search history.

(56) References Cited

U.S. PATENT DOCUMENTS

| | | | | |
|---|---|---|---|---|
| 4,456,005 | A * | 6/1984 | Lichty | A61B 17/8685 606/315 |
| 4,653,244 | A * | 3/1987 | Farrell | E04F 13/0837 411/399 |
| 4,978,350 | A * | 12/1990 | Wagenknecht | A61B 17/8635 411/387.7 |
| 5,334,204 | A * | 8/1994 | Clewett | A61B 17/8625 606/312 |
| 5,498,265 | A * | 3/1996 | Asnis | A61B 17/74 606/315 |
| 6,030,162 | A * | 2/2000 | Huebner | A61B 17/1682 411/263 |
| 6,306,140 | B1 * | 10/2001 | Siddiqui | A61B 17/863 606/315 |
| 6,666,638 | B2 * | 12/2003 | Craven | F16B 5/0275 411/387.2 |
| 6,966,737 | B2 * | 11/2005 | McGovern | F16B 5/0275 411/387.2 |
| 7,090,452 | B2 * | 8/2006 | Chen | F16B 25/0031 411/387.1 |
| 8,273,113 | B2 * | 9/2012 | Frenk | A61B 17/863 411/412 |
| 2004/0210227 | A1 * | 10/2004 | Trail | A61B 17/863 606/916 |

FOREIGN PATENT DOCUMENTS

| | | |
|---|---|---|
| JP | 2017094197 A | 6/2017 |
| WO | WO-2007090151 A1 | 8/2007 |
| WO | WO-2009009521 A2 | 1/2009 |

OTHER PUBLICATIONS

U.S. Appl. No. 13/040,066, U.S. Pat No. 8,740,955, filed Mar. 3, 2011, Bone Screw With Multiple Thread Profiles for Far Cortical Locking and Flexible Engagement to a Bone.

U.S. Appl. No, 14/265,662, U.S. Pat. No. 9,314,286, filed Apr. 30, 2014, Bone Screw With Multiple Thread Profiles for Far Cortical Locking and Flexible Engagement to a Bone.

"European Application Serial No. 16192273.7, Extended European Search Report dated Mar. 15, 2017", 7 pgs.

"Japanese Application Serial No. 2013-555794, Response filed Jul. 26, 2016 to Notice of Reasons for Rejection dated Jan. 26, 2016", (W/ English Translation), 12 pgs.

"Japanese Application Serial No. 2017-018547, Office Action dated Nov. 28, 2017", With English Translation, 6 pgs.

"Japanese Application Serial No. 2017-018547, Response filed May 24, 2018 to Office Action dated Nov. 28, 2017", (W/ English Translated Claims), 10 pgs.

* cited by examiner

BONE SCREW WITH MULTIPLE THREAD PROFILES FOR FAR CORTICAL LOCKING AND FLEXIBLE ENGAGEMENT TO A BONE

CROSS-REFERENCE TO RELATED APPLICATIONS

This is a continuation-in-part of U.S. patent application Ser. No. 11/058,935, filed Feb. 15, 2005, the contents of which is incorporated by reference herein in its entirety.

FIELD OF DISCLOSURE

The present disclosure relates generally to the field of medical devices. In particular, embodiments of the present disclosure relate, but are not limited, to a bone screw with features and/or attributes to provide positive-locking but flexible engagement to a bone. Even more particularly, the present disclosure relates to bone plate systems, including the bone screws used therewith, that are less stiff (as compared to existing systems) and thereby promote effective and substantially more uniform callus formation at the fracture site during initial bone healing.

BACKGROUND

Bone screws have typically been used to directly compress osteosynthesis plates onto the bone in order to align and stabilize a bone fracture. In this utilization, bone screws are not fixed rigidly to the bone plate, and the resulting frictional force between the plate and the bone is solely responsible for the stability of the osteosynthesis construct. Loosening of the screws in the bone or a resorption of the bone can thus easily lead to a loss of stability.

To avoid such loosening, and for the purpose of improving vascularity in a manner that minimizes damage to the bone surface, means for rigid locking of a bone screw in a bone plate and elevated fixation of a bone plate over the bone surface have been introduced. For example, in one prior art implementation, a positive-locking system between the screw and plate is effectuated by means of a bone plate with conical plate holes. The conical plate holes provide a rigid connection between the plate and the fixation screws, even after the screw-bone interface has loosened. In another prior art implementation, a positive-locking system effectuated by fitting screw holes in the plate with inside threads. These threaded holes accept bone screws fitted with a second threaded portion which is widened compared to the conventional threaded screw shank segment, to facilitate engagement with the inside thread of the plate hole. These prior art positive-locking screws are designed to be threaded into the first bone surface underlying the plate, or into both the first and second bone surface of a quasi-cylindrical bone cross-section underlying the plate.

While these positive-locking osteosynthesis constructs provide superior stability, their stiffness can pose increased stress to the screw-bone interface. This has introduced failure modes, in which the bone resorbs or fractures adjacent to the outermost screw in the plate, since this screw absorbs the majority of the stress as the load is transferred from the bone to the plate.

Furthermore, the stiffness of the fixation construct suppresses small motion at the fracture site, which otherwise can be beneficial for fracture healing by inducing a fracture callus. Less stiff external fixators similarly impose positive-locking between bone pins and an external fixation bar. However, flexion of the considerably long fixation pins allows for controlled motion at the fracture site that is of sufficient magnitude to induce fracture healing by callus formation. While positive-locking plate-screw constructs employ a similar fixation principle as an external fixator, the close proximity of the plate to the bone surface prohibits elastic flexion of the screw segment between the plate and the bone.

SUMMARY

In one aspect, the present disclosure is directed to a bone screw having a head portion and a shaft portion. The shaft portion includes a proximal neck section, a threaded mid-section and a threaded front section distal to said mid-section. The mid-section has a thread profile different from the thread profile of the front section and the threaded front section is configured for engaging cortical bone.

In another aspect, the present disclosure is directed to a bone plate and bone fastener system. The system includes a metal plate having an elongated body including a first end and a second end. The plate body defines a plurality of apertures extending therethrough. The system further includes a plurality of fasteners wherein at least one of said fasteners has a head portion and a shaft portion. The shaft portion has an unthreaded neck section, a threaded mid-section, and a threaded front section distal to said mid-section. The threaded front section is configured to engage the far cortical wall of a bone. The mid-section has a thread profile different from the thread profile of the front section.

In yet another aspect, the present disclosure is directed to a method for treating a bone fracture with an osteosynthesis construct. The method includes determining, by diagnostic means, one or more of the size of the bone and/or the thickness of the cortical wall. The method further includes selecting a metal plate comprising an elongated body having a first end and a second end. The plate body further includes a plurality of apertures extending therethrough. The method further includes aligning at least a section of the elongated body with the diaphysis of the bone to bridge the fracture site. A screw for attaching the plate to the diaphysis is selected. The screw has a shaft including an unthreaded neck section, a threaded mid-section, and a threaded front section distal to the mid-section. The selection of the screw is based at least on the thickness of said cortical wall. The method further includes providing a pilot hole in at least the near cortex of the bone, wherein the diameter of said pilot hole is greater than the diameter of screw neck portion. The screw is then advanced so that substantially the entire front section of the screw engages the far cortex of the bone and substantially no part of the threaded mid-section engages any bone during the far cortical engagement.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Illustrative embodiments of the present disclosure include, but are not limited to, a bone screw, an osteosynthesis construct, and associated methods for using the bone screw and/or the osteosynthesis construct.

Various aspects of the illustrative embodiments will be described using terms commonly employed by those skilled in the art to convey the substance of their work to others skilled in the art. However, it will be apparent to those skilled in the art that alternate embodiments may be practiced with only some of the described aspects. For purposes of explanation, specific numbers, materials, and configurations are set forth in order to provide a thorough understanding of the illustrative embodiments. However, it will be apparent to one skilled in the art that alternate embodiments may be practiced without the specific details. In other instances, well-known features are omitted or simplified in order not to obscure the illustrative embodiments.

The phrase "in one embodiment" is used repeatedly. The phrase generally does not refer to the same embodiment; however, it may. The terms "comprising", "having" and "including" are synonymous, unless the context dictates otherwise.

The terms "minor" and "core" when used to describe a diameter of a screw or screw shaft are used interchangeably and have the same meaning.

Figure 1:
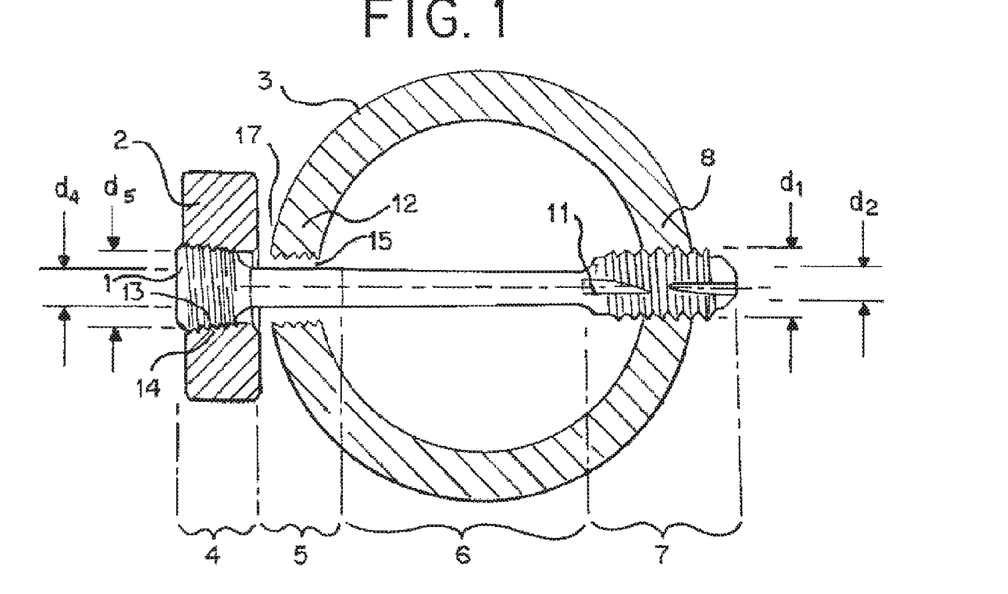
FIG. 1 shows a side-view of a bone screw, in accordance with one aspect and some embodiments disclosed herein, in association with a transverse cross-section of a tubular bone segment and a bone plate.

Referring now to FIG. 1, illustrated therein is bone screw 1 in accordance with various embodiments and one aspect of the present invention. Additionally, bone screw 1 is illustrated with a cross sectional view of tubular bone 3 and bone plate 2. As illustrated, for the embodiments, bone screw 1 includes a head portion 4 and an adjoining shaft portion having a front section 7, a mid-section 6, and a neck section 5. As will be described in more detail below, in various embodiments, at least two of sections 5-7 are endowed with complementary features and/or attributes, such that bone screw 1 may be positively-locked, but flexibly engaged to a bone. Additionally, bone screw 1 may be employed in conjunction with bone plate 2 to form an osteosynthesis construct. Further, potential advantages that may be obtained from adapting, and using bone screw 1 will also be described below.

For the embodiments, bone screw 1 is a rotationally symmetrical unitary piece having a central axis, depicted by the dotted line running from head portion 4 through the neck, mid and front sections 5-7 of the shaft portion. In various embodiments, bone screw 1 is made of a biocompatible material, e.g. stainless steel or titanium.

For the illustrated embodiments, front section 7 has a core diameter of d1, and is threaded for secure fixation of bone screw 1 in the far bone surface, termed far cortex 8. The length of threaded front section 7 is sufficient to span or exceed the thickness of far cortex 8.

Further, for the illustrated embodiments, threaded front section 7 may incorporate a self-tapping feature 9, which allows for insertion of bone screw 1 without the need for tapping of a screw thread. Additionally, for the illustrated embodiments, threaded front section 7 may also incorporate a self-drilling feature 10, which allows for screw insertion without the need for pre-drilling a hole in the cortex. Still further, for the illustrated embodiments, threaded front section 7 may also incorporate a second self-drilling feature 11 located toward mid-section 6, which allows for screw removal (withdrawal) to penetrate newly formed bone at the perimeter of the screw hole (cavity) 15 in the near cortex 12. The term "screw hole" is also referred to herein as "pilot hole." The terms "screw hole" and "pilot hole" both refer to the element in the Figures identified by reference numeral 15. These terms are used interchangeably and have the same meaning.

Still referring to FIG. 1, mid-section 6 of the shaft portion has a diameter d2. The diameter d2 may be constant, or may alter towards the neck section 5 in a manner to induce essentially evenly distributed bending and strain along midsection 6 as a load perpendicular to the central axis of bone screw 1 is applied to head portion 4 of bone screw 1. The diameter d2 may be as large as the core diameter of the threaded front section, but may be smaller and may be as small as 50% of the core diameter of the threaded front section 7. Additional examples of bone screw 1 wherein the core diameter of mid-section 6 is smaller than the core diameter of front section 7 are also disclosed with reference to FIGS. 5-18. The length of mid-section 6 extends through a substantial portion of the distance between the near and far cortex.

The geometry of mid-section 6 effectively determines the stiffness for the connection between bone 3 and bone plate 2. In various embodiments, the geometry is selected such that mid-section 6 has a bending ability to accommodate flexion along the central axis of bone screw 1, to allow for controlled relative motion between bone 3 and bone plate 2. In various embodiments, the bending ability is sufficient to accommodate excessive loading of the osteosynthesis construct. In such event, mid-section 6 provides for a controlled failure mechanism to delay or prevent more detrimental failure modes, such as plate bending or bone fracture. Further, this elasticity may also improve the ability of head portion 4 to engage bone plate 2, especially for embodiments where engagement involves engaging threads 13 of head portion 4 with threaded through hole 14 of bone plate 2, and the "screw holes" in the bone and threaded through hole 14 of bone plate 2 are not precisely concentric.

The exact geometric attributes of mid-section 6 is application dependent, that is, it may vary from one application to another. Further, for the illustrated embodiments of FIGS. 1-4, mid-section 6 is illustrated as being unthreaded. In alternate embodiments, mid-section 6 may be threaded instead. Examples of such alternative embodiments where mid-section 6 is threaded are described in greater detail below with particular reference to FIG. 5-18.

Continuing to refer to FIG. 1, neck section 5 has a core diameter of d4 and spans the width of near cortex 12 without being rigidly fixed in near cortex 12, with near cortex 12 being the bone surface underlying bone plate 2. The diameter d4 may be as large as the core diameter of threaded front section 7, and may be as small as 50% of the core diameter of threaded front section 7. The diameter d4 is smaller than the diameter d5 of screw hole 15 in the near cortex. The difference between d4 and d5 determines the amount of flexion the screw shaft will accommodate before neck section 5 contacts screw hole 15 in near cortex 12.

The resulting axial and translational degree of freedom between screw neck 5 and screw hole 15 in the near cortex plays a significant role in realizing the benefits of far cortex fixation, including reduction of construct stiffness and reduction of stress concentrations at the screw-bone interface. In addition, the resulting axial and translational degree of freedom also relates to the degree of bone movement of the two bone segments at the fracture site relative to each other, and consequently to the effective and substantially uniform callus formation at the site. Contact of the screw shaft with near cortex 12 due to increased loading of the osteosynthesis construct may provide additional support, and may dynamically increase construct stiffness.

Figure 2:
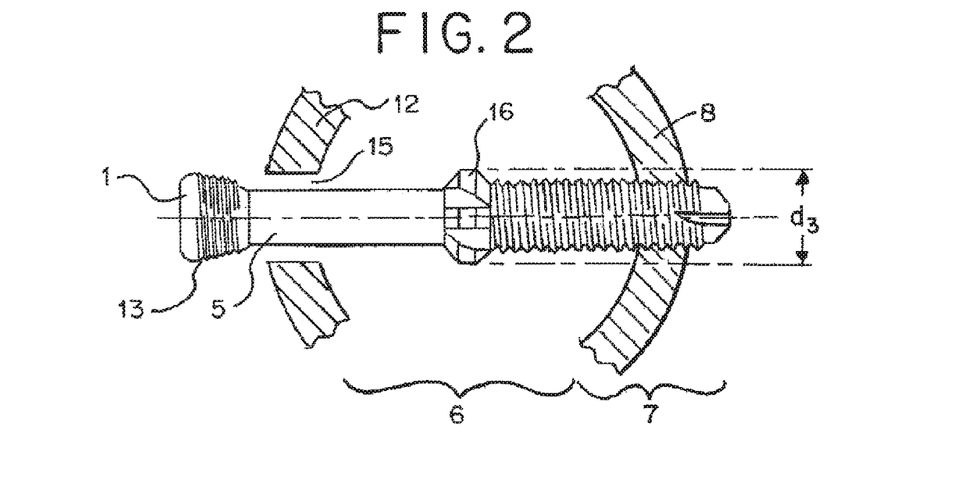
FIG. 2 shows a side-view of the bone screw, in accordance with other embodiments.

Referring now also to FIG. 2, wherein various alternate embodiments of bone screw 1 are illustrated. For these alternate embodiments, instead of the reduced neck diameter design shown in FIG. 1, alternative means to achieve the desired degree of freedom between the neck section 5 and near cortex 12 are employed. For the embodiments, mid-section 6 is provided with a short, elevated cutting flute 16 of diameter d3. The diameter is at least as big as the outer diameter of threaded front section 7, and may be up to twice as big as the outer diameter of threaded front section 7. A screw shaft having a portion of an increased diameter (e.g., core diameter) with a cutting element such as cutting flute 16 may also be provided with a bone screw 1 wherein the core diameter of neck section 5 and the core diameter of mid-section 6 are smaller than the core diameter of front section 7. Such embodiments are discussed in greater detail below. Thus, during screw insertion, cutting flute 16 will further expand the diameter of screw hole 15 in near cortex 12, initially established with a smaller diameter for allowing front section 7 to pass through, to ensure that neck section 5 of bone screw 1 is not rigidly fixed in near cortex 12. During screw removal/withdrawal, cutting flute 16 may again expand screw hole 15 in near cortex 12 to remove newly formed bone.

Referring now to both FIGS. 1 and 2 as well as FIGS. 5-18, for the illustrated embodiments, head portion 4 is provided with a conical shape, and in some embodiments is fitted with a threaded portion 13. In various embodiments, thread portion 13 is widened, compared to the threads of front section 7. This threaded head is adapted to engage with the inside thread that partially defines plate hole or aperture 14 in bone plate 2 to form a positive-locking mechanism between bone screw 1 and bone plate 2. In other embodiments disclosed herein, head portion 4 may be unthreaded. For example, as shown and described in more detail below in connection with FIGS. 5, 7-11 and 17-18, head portion 4 may be unthreaded and spherical. Bone screws of this type may be further provided with cap 48 that has an external thread adapted to engage an internal thread within aperture 14 of a corresponding bone plate 2, as will be recognized by those of skill in the art. Notwithstanding such differences, for purposes of the present disclosure, the same reference numerals are otherwise used in the various embodiments to refer to similar elements or features of the bone screw, the plate or the entire system or construct. Use of the same reference numerals, such as numeral "1" for the bone screw and numeral "2" for the bone plate is not intended to suggest that the screws, plates and constructs do not differ in other respects.

Also, while the foregoing descriptions have been presented with bone screw 1 and plate 2 illustrated in the context of a cross-section of a tubular bone. Those skilled in the art will appreciate that the present invention is not so limited, and may be practiced in non-tubular situation.

Still referring to FIGS. 1-2, in various applications, bone screw 1 is inserted through bone plate 2 into bone 3. More specifically, in various applications, bone screw 1 is inserted substantially perpendicular to the surface plane of bone plate 2, and is substantially aligned with the central axis of the plate hole of bone plate 2. During screw insertion, bone plate 2 may or may not be elevated from the bone surface 17. Screw insertion will terminate as soon as the threaded screw head section 4 is fully seated in the corresponding threaded plate hole 14. After screw insertion, bone plate 2 is positively locked to bone screw 1, and will maintain the elevation from the bone surface given during screw insertion.

In various applications/embodiments, two or more far cortex bone screws 1 of FIGS. 1-2 may be associated with bone plate 2 to form an osteosynthesis construct. The stiffness of the construct may be adjusted by the complementary geometry provided to the bone screws 1, and by the number of bone screws 1.

In other applications/embodiments, one or more far cortex bone screws 1 of FIGS. 1-2 may be combined with one or more conventional positive-locking bi-cortical or near cortex bone screws to provide for a more gradual load transfer between the bone and the bone plate. Bi-cortical locking screws are screws that engage the bone at both the near cortex 12 and far cortex 8. Thus, bi-cortical locking screws will typically include screw threads (or other engagement means) at least at the distal end of the screw shaft and the proximal end of the screw shaft. Indeed, bi-cortical locking screws are often threaded along the entire length of the screw shaft. Inasmuch as bi-cortical locking screws engage or are otherwise rigidly fixed within the near cortex (in addition to the far cortex), the neck section within the pilot hole 15 does not move either by virtue of a smaller shaft diameter and/or expanded pilot hole diameter. More typically, however, in most applications where far cortical locking is utilized and a less stiff osteosynthesis construct is desired, all of the bone screws extending through the diaphysis are bone screws of the type described herein, namely, bone screws that only engage far cortex 8 and allow for limited movement of neck section 5 within the near cortex 12.

In still other applications/embodiments, one or more far cortex bone screws 1 of FIGS. 1-2 may be combined with one or more conventional, non-locking bi-cortical screws to improve fixation strength and durability.

Figure 3:
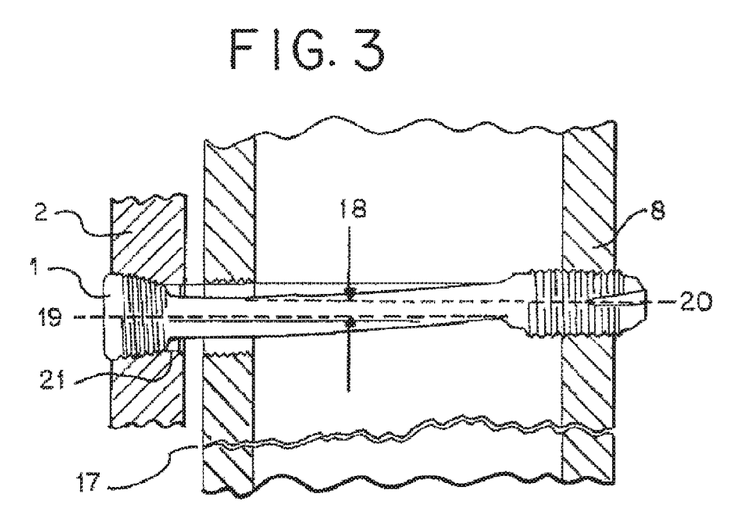
FIG. 3 shows a method for attaching a bone screw to a bone, using an embodiment of the bone screw of FIGS. 1-2, in accordance with another aspect and other embodiments of the present disclosure.

FIG. 3 demonstrates another implementation/application of far cortex locked screw 1 for compression of a bone fracture 17. For the implementation/application, far cortex locked screw 1 is employed to provide an offset 18 between the plate hole axis 19 and the axis 20 of the screw hole in the far cortex. To achieve compression at the fracture site 17 that is spanned by the osteosynthesis construct, bone screw 1 can be inserted in the far cortex 8 parallel to the axis of the corresponding plate hole and fracture site 17, but slightly further away from the fracture site 17 as compared to the axis of corresponding plate hole. This non-concentric screw insertion is made possible by the elastic bending ability of the screw shaft to engage the screw head into the threaded plate hole. This in turn transmits prolonged compression to fracture site 17 due to the elastic force stored in the screw shaft.

The offset between the screw hole axis 20 in far cortex 8 and the corresponding plate hole axis 19 may be in the range of 1 mm to 5 mm. Screw insertion in the far cortex under such offset may be accommodated since the screw neck is smaller in diameter than the near cortex screw hole and the plate hole 21.

Figure 4:
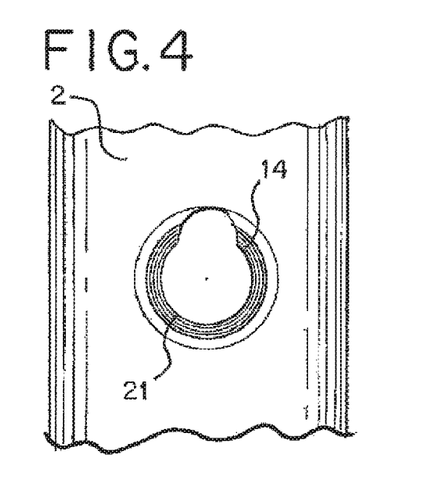
FIG. 4 shows a top view of a plate hole in accordance with other embodiments, and another aspect of the present disclosure, suitable for use to practice the method of FIG. 3.

In various embodiments, if a larger offset is desirable, the plate hole 21 may be adapted by elongating the hole in direction of the longitudinal plate axis, and towards the end of the plate, as depicted in FIG. 4. In other words, a portion of the circumference of the substantially circular plate hole 21 may be extended in the desired direction.

With reference to FIGS. 5-18, described below are additional embodiments of bone screws that provide uni-cortical engagement, that is, engagement of bone screw 1 with only the far cortex 8 while allowing neck section 5 a limited range of motion within pilot (or screw) hole 15 in the near cortex 12. Thus, like the embodiments of FIGS. 1 and 2, the alternative embodiments described below include a threaded front section 7 for engaging far cortex 8. Also, as described in connection with the embodiment of FIG. 1, mid-section 6 has a stiffness and a bending ability that can accommodate a degree of flexion along the central axis of bone screw 1, thereby providing a osteosynthesis construct of less stiffness (when compared to systems that employ screws for bi-cortical engagement). Furthermore, the embodiments described below include a mid-section 6 that is likewise threaded (as also disclosed above in connection with the embodiment of FIG. 1), but still maintains the desired bending ability.

Figure 5:
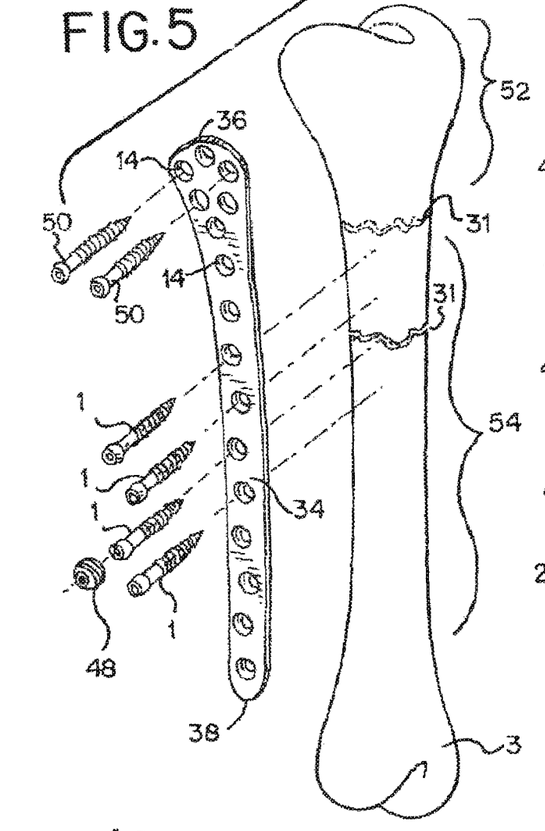
FIG. 5 is a perspective view of a bone plate construct applied to a fractured bone including one embodiment of a bone screw of the present disclosure in relation to two alternative or cumulative fracture sites.
Figure 6:
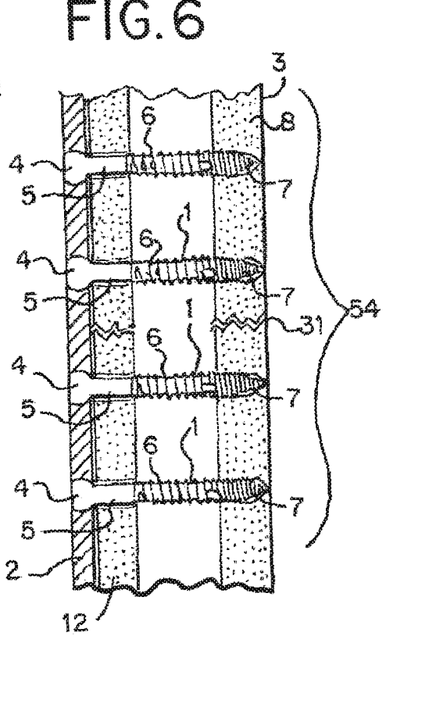
FIG. 6 is a cross-sectional side view of the bone plate (osteosynthesis) construct attached to a fractured bone with bone screws of the present disclosure on both sides of the fracture site.

Turning first to FIGS. 5-6, an exemplary osteosynthesis construct useful in the treatment of bone fractures and particularly in the secondary healing through callus formation at the fracture site 31 is shown. The bone construct includes plate 2 and one or more types of bone screws, including one or more of bone screw 1 of the present disclosure. As shown in FIG. 5, plate 2 includes an elongated body 34 having a first end 36 and a second end 38. Plate 2, which is typically made of a metal such as, but not limited to, titanium, stainless steel, or alloys thereof, is preferably anatomically contoured for conforming placement against bone 3. As shown in FIG. 5, plate 2 may include a widened or laterally extending portion at the first (e.g., proximal) end 36 or at the second (e.g., distal) end 38, for contact with the metaphysis or epiphysis of bone 3. The remainder of plate 2 is aligned against the diaphysis of bone 31, so as to bridge fracture site 31. Of course, plate(s) 2, may be provided in different shapes and sizes as necessary. Bone plates 2 for treating fractures of different long bones, including the femur, tibia and humerus, and that are useful in the systems and methods disclosed herein are available from Zimmer, Inc., of Warsaw, Ind.

As discussed above and shown in FIGS. 5 and 6, the bone plate system typically includes a plurality of bone screws 1 for engaging the far cortical wall (far cortex 8) of bone 3. In addition to screws of the type described herein, additional bone screws for engaging other parts of the bone and different bone types may also be included in the surgical procedure. For example, bone screws 50 for engaging cancellous bone at, for example, the metaphysis or epiphysis of the bone may also be employed in combination with bone screws of the present disclosure intended for engagement of the far cortex 8. Cancellous bone is sometimes referred to as "spongy bone" and has a more open structure than the more dense cortical bone. Thus, cancellous bone screws may have a different thread profile (as that term is defined below) than the thread profile of bone screw 1. Use of cancellous bone screws 50 and placement of such screws in combination with bone screws 1 of the present disclosure will depend, in part, on the number and location of the fracture sites 31 and/or 31'. Placement of bone screws 1 described herein relative to other screws and fracture sires 31 or 31' is discussed in more detail below. The plate(s) and different types of screws, i.e., screws for engaging cancellous bone and screws for engaging the far cortex 8 may be provided as a single kit, with (optionally) the tools required to attach the same and other accessories such as spacers, locking caps and the like.

Figure 7:
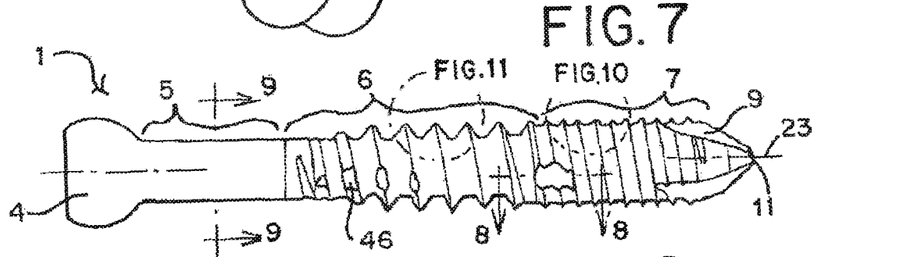
FIG. 7 is a side view of one embodiment of a bone screw of the present disclosure.

Turning now to FIG. 7, there is shown another embodiment of bone screw 1 for use with bone plate 2, wherein the bone screw 1 is adapted or configured for attachment to the far cortex 8. As shown in FIG. 7, bone screw 1 includes a head portion 4, neck section 5, mid-section 6, and front section 7. Bone screw 1 may be made of any metal suitable for use with bone, such as the previously mentioned titanium, stainless steel, and alloys thereof. One such alloy is a titanium-vanadium-aluminum alloy, known commercially as TIVANIUM®. Ti-6Al-4V alloy, which is used and available in osteosynthesis products sold by Zimmer, Inc of Warsaw, Ind. The surface of bone screw 1 may be treated by zirconia bead blast or other surface treatment techniques, which may improve the fatigue strength and provide other desirable properties to bone screw 1.

Inasmuch as the bone size among different patients will vary, bone screw 1 is preferably dimensioned to allow for its use in a range of bone sizes and bone types. Thus, bone screw 1 may come in a variety of lengths and diameters to allow for use with different bones (e.g., femur, tibia, humerus) as well as different bone sizes of the same. Typically, but without limitation, bone screw 1 will have a diameter of anywhere between 3.0 mm and 6.0 mm measured at the largest major diameter of bone screw shaft. More specifically, bone screw 1 may have a major diameter of approximately 3.0 mm, 3.5 mm, 4.0 mm, 4.5 mm, 5.0 mm, up to approximately 6.0 mm.

Similarly, bone screw 1 may have any desirable length and more specifically any length that allows for substantially full engagement with the far cortex 8. In one embodiment, bone screw 1 will have a length between approximately 20 and 70 mm. For example, bone screw 1, for use with tibial and humeral plates may, in one embodiment, have a length between approximately 20 mm and approximately 60 mm when the largest major diameter is in the range of about 3.5 mm to 4.5 mm and, more preferably, approximately 4.0 mm. Bone screw 1, for use in a femoral plating construct may, depending on the material, be larger and have a length of between about 30 mm to about 60 mm, with a largest major diameter of approximately between 4.5 and 5.5 mm and, more typically, approximately 5.0 mm. The selection of the bone screw required for a given surgical procedure is made by the physician after examination of the patient's bone size and other bone characteristics by X-ray or other diagnostic means.

As noted above, bone screw 1 will typically include a threaded front section 7. The threads of front section 7 are configured to, among other things, fixedly engage cortical bone and in particular the far cortical bone 8. As in the previously described embodiments, threaded front section 7 terminates in a pointed distal tip 11 and may incorporate a self-tapping element 9, which allows for insertion without the need for tapping a screw thread. Optionally, front section 7 may also have a self-drilling element (as described in connection with the embodiment of FIG. 1) although more typically a pilot hole is provided by using a dedicated drilling tool as will be known to those of skill in the art.

As disclosed above, mid-section 6 may also be threaded. Inasmuch as the bone constructs described herein are intended to be temporary and are removed once the bone has healed, in one embodiment, mid-section 6 may include a reverse thread to allow for more effective removal of bone screw. Also, in that regard, mid-section 6 may preferably include one or more cutting flutes 46 as shown in FIG. 7 and also in FIG. 9 to further assist in screw removal. Cutting flutes 46 may be equally spaced about central axis 23 of bone screw 1. In one embodiment, 3 sets of cutting flutes equally spaced about the central axis 23 of bone screw 1 in mid-section 6 are provided.

Typically, mid-section 6 will have a different thread profile than the thread profile of front section 7. By "different thread profile," it is meant that the thread form of mid-section 6 and front section 7 differ in one or more respects, such as, major diameter, minor or core diameter, length of the threaded section, thread pitch, thread angle, shape and angle of the thread root, and the like. Thus, for example, as shown in FIG. 7, and in more detail in FIGS. 8-11, the threaded portion of front section 7 has a larger core diameter $d_f$ than the diameter $d_m$ of mid-section 6. By providing mid-section 6 with a reduced minor/core diameter $d_m$ relative to the core diameter $d_f$ of front section 7, mid-section 6 retains its desired bending properties and simultaneously provides means for effective removal of screw 1.

The relative lengths of front section 7, mid-section 6, and neck section 5 are selected to achieve desired objectives of far cortical locking including, among others, flexion without failure at the mid-section 6 and range of motion for neck section 5 within the near cortex. Thus, the relative lengths may be substantially identical, similar, or may vary as needed. More particularly, the relative lengths of front section 7, mid-section 6 and neck section 5 are selected to accommodate different bone sizes and bone characteristics so that when bone screw 1 is fully implanted (1) the far cortex is at least substantially engaged by front section 7, (2) no part or at least substantially no part of mid-section 6 engages any part of the near or far cortex, (3) the stiffness of mid-section is sufficient to provide the desired bending ability under expected axial loading, (4) mid-section 6 quickly engages the near cortex upon screw removal, (5) substantially all of neck section 5 resides within pilot (screw) hole 15 and (6) neck section 5 enjoys a sufficient clearance on either side to allow for a limited degree of motion. With regard to pilot hole 15 clearance, in accordance with the present disclosure, a gap of between approximately 0.2 mm and 0.6 mm and more typically approximately 0.5 mm on either side of neck section 5 within the near cortex may be desirable in most applications.

Set forth below in Tables 1 and 2 are listings of certain exemplary bone screws in accordance with the present disclosure and more particularly bone screw 1 of FIG. 7 with, among other things, the relative lengths of neck section 5, mid-section 6 and front section 7 for a bone screw 1 having a selected major diameter ($d_{maj}$). The listings provided below are not intended to be exhaustive or limit the scope of the invention in any way. In any event, bone screws 1 listed in Table 1 are typically made of a titanium having a mid-section 6 with a major diameter of approximately 4.85-5.0 mm; a mid-section 6 minor diameter of approximately 3.05-3.2 mm, a neck section diameter of approximately 3.35-3.45 mm; a front section minor diameter of approximately 4.25-4.4 mm; and a front section major diameter of approximately 4.85-5.0 mm. The screws listed in Table 1 are intended for use with a pilot hole diameter in the near cortex of approximately 3.35-3.45 mm to provide a neck section 5/pilot hole clearance of approximately 0.416-0.475 mm on either side of the neck section 5.

TABLE 1

| $d_{maj}$/Length (mm) | Neck Section (mm) | Mid-Section (mm) | Front Section (mm) |
| --- | --- | --- | --- |
| 5.0/30 | 5 | 11 | 10 |
| 5.0/32 | 6 | 12 | 10 |
| 5.0/34 | 7 | 13 | 10 |
| 5.0/36 | 8 | 14 | 10 |
| 5.0/38 | 8 | 13 | 13 |
| 5.0/40 | 8 | 15 | 13 |
| 5.0/42 | 8 | 17 | 13 |
| 5.0/44 | 8 | 19 | 13 |
| 5.0/46 | 8 | 21 | 13 |
| 5.0/48 | 8 | 23 | 13 |
| 5.0/50 | 8 | 25 | 13 |
| 5.0/52 | 8 | 27 | 13 |
| 5.0/54 | 8 | 29 | 13 |
| 5.0/56 | 8 | 31 | 13 |
| 5.0/58 | 8 | 33 | 13 |
| 5.0/60 | 8 | 35 | 13 |

The screws listed in Table 2 are typically made of a TIVANIUM® alloy having a mid-section 6 with a major diameter of approximately 3.85-4.0 mm; a mid-section 6 minor diameter $d_m$ of approximately 2.45-2.6 mm; a neck section 5 diameter of approximately 2.45-2.6 mm; a front section 7 minor diameter of approximately 3.25-3.4 mm; a front section major diameter of approximately 3.85-4.0 mm. The screws listed in Table 2 are intended for use with a pilot hole diameter in the near cortex of approximately 3.28-3.3 mm to provide a neck section 5 pilot hole clearance of 0.341-0.425 mm on either side of the neck section 5.

TABLE 2

| $d_{maj}$/Length (mm) | Neck Section (mm) | Mid-Section (mm) | Front Section (mm) |
| --- | --- | --- | --- |
| 4.0/24 | 6 | 5 | 8 |
| 4.0/26 | 7 | 6 | 8 |
| 4.0/28 | 7 | 7 | 9 |
| 4.0/30 | 7 | 8 | 10 |
| 4.0/32 | 7 | 10 | 10 |
| 4.0/34 | 8 | 11 | 10 |
| 4.0/36 | 9 | 12 | 10 |
| 4.0/38 | 9 | 11 | 12 |
| 4.0/40 | 9 | 13 | 12 |
| 4.0/42 | 9 | 15 | 12 |
| 4.0/44 | 9 | 17 | 12 |
| 4.0/46 | 9 | 19 | 12 |

Figure 8:
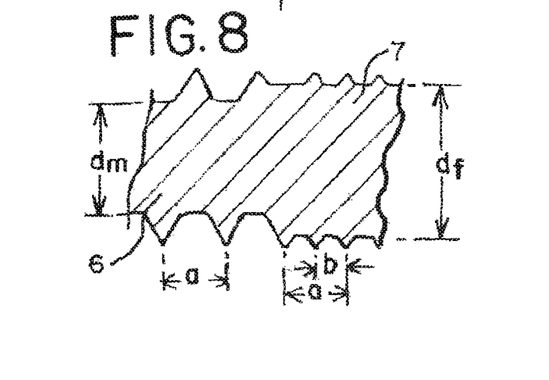
FIG. 8 is an enlarged cross-sectional view of the bone screw of FIG. 7 taken along line 8-8 and showing the thread profile at the junction of the mid-section and front section of the shaft.
Figure 9:
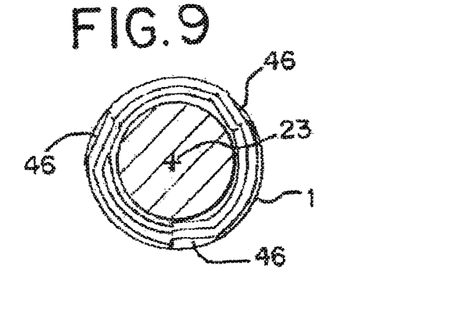
FIG. 9 is a cross-sectional end view of the bone screw of FIG. 7 taken along line 9-9.

Other differences in the thread profiles of mid-section 6 and front section 7 may include the thread pitch. As shown in FIGS. 7 and 8, front section 7 may include a double lead thread form. Thus, the pitch "a" (distance between adjacent thread crests) of mid-section 6 may, for example, be twice that of the pitch "b" of front section 7 as shown in FIG. 8. Although the thread pitch "a" of mid-section 6 and front section 7 need not differ and may be identical, a finer pitch within front section 7 may provide for more rapid advancement of bone screw 1 into the more dense cortical bone.

Figure 10:
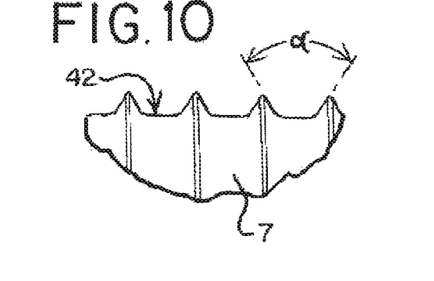
FIG. 10 is an enlarged side view of the thread profile of the mid-section of the bone screw shown in FIG. 7.
Figure 11:
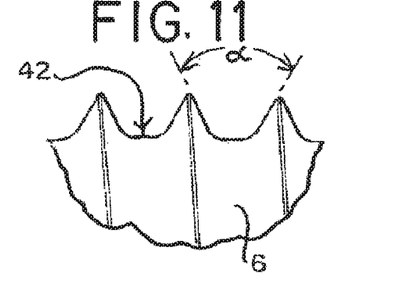
FIG. 11 is an enlarged side view of the thread profile of the front section of the bone screw shown in FIG. 7.

FIGS. 10-11 show additional aspects of the thread profiles of mid-section 6 and front-section 7. For example, thread angle α of both threaded portions may be identical (e.g., 60°) and at least substantially symmetrical, while the roots 42 of the threads within the respective sections 6 and 7 may differ. For example, as shown in FIGS. 10-11, the more shallow thread root 42 of front section 7 may have a flatter profile than the deeper thread root 42 of mid-section 6, which is more to roidal in its profile.

Figure 12:
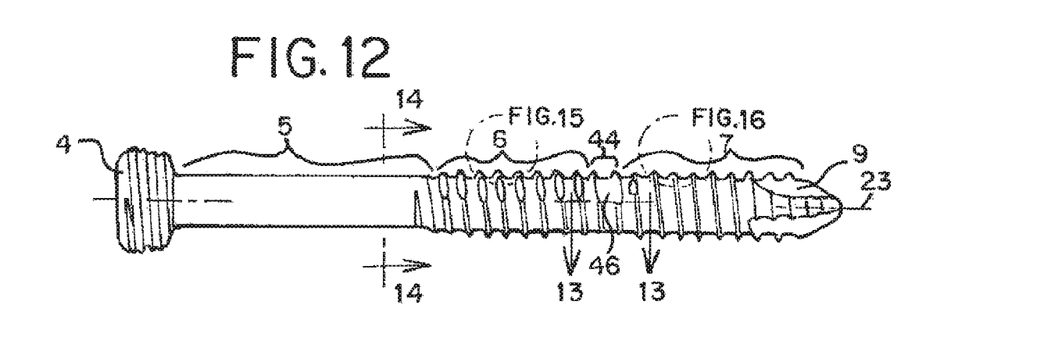
FIG. 12 is a side view of another embodiment of a bone screw of the present disclosure.

Turning now to FIG. 12, there is shown a further alternative embodiment of bone screw 1. As with the bone screw shown in FIG. 7, bone screw 1 of FIG. 12 likewise includes a threaded front section 7 and a threaded mid-section 6. As in the embodiment of FIGS. 7-11, bone screw 1 of FIGS. 12-16 may have any desirable length and more preferably any length that allows for substantially full engagement with the far cortex 8. In one embodiment, bone screw 1 will have a length between approximately 20 and 70 mm. For example, bone screw 1, for use with tibial and humeral plates may, in one embodiment, have a length between 20 mm and approximately 60 mm with an outer diameter in the range of about 3.0 mm to 4.0 mm and, more preferably, approximately 3.5 mm. Bone screw 1, for use in a femoral plating construct, may likewise have a length of approximately 20-60 mm and have a larger diameter of between approximately 4.0 and 5.0 mm and, more typically, approximately 4.5 mm.

Threaded front section 7 and threaded mid-section 6 of bone screw 1 shown in FIGS. 12-16 may also differ in their thread profiles. As in the embodiment previously described, mid-section 6 may have a smaller core diameter $d_m$ than the core diameter $d_f$ of front section 7. As in the preceding examples, the core diameter of mid-section 6 should provide the shaft of screw 1 with sufficient strength and still maintain the desired bending ability when subjected to different axial loads. For example, where bone screw 1 has a major diameter of approximately 3.5 mm, mid-section 6 may have a minor/core diameter $d_m$ of between approximately 2.5 mm and 2.7 mm while front section 7 may have a minor/core diameter $d_f$ of between approximately 2.7 mm and 2.8 mm. In a bone screw having a larger major diameter, such as approximately 4.5 mm, the core diameters of the mid-section 6 and front section 7 may be between approximately 3.1 mm and 3.3 mm and 3.4 mm and 3.5 mm, respectively. Of course, the dimensions of any screw may further depend on the material of the screw. Thus, the exemplary dimensions identified above are more typical of bone screws made of materials that are more stiff than the above described titanium and titanium alloys, such as, but not limited to, stainless steel.

Bone screw 1 shown in FIGS. 12 and 13-16 may further include an expanded core portion 44 typically located between mid-section 6 and front section 7. As shown in greater detail in FIG. 13, expanded core portion 44 has a minor/core diameter that is greater than the minor/core diameter of mid-section 6 and/or front section 7. In addition, expanded core portion 44 may include a cutting element 46, such as cutting flutes spaced about the screw central axis 19 as seen in FIG. 12. Like the enlarged collar portion described above in the embodiment of FIG. 2, expanded core portion 44 allows for expansion of pilot hole 15 in the near cortex 12 in order to accommodate movement of neck portion 5 within the pilot hole as previously described. Bone screw 1 with an expanded core section 44 and cutting element 46 is particularly advantageous in bone plate attachment procedures where the initial pilot hole, while large enough to accommodate front section 7 does not provide the sufficient clearance at the near cortex to accommodate movement of neck section 5 within pilot hole 15.

By providing the expanded core portion 44 on the shaft of the screw itself, the pilot hole may be expanded to the desired diameter without the need for a separate drilling tool or drilling step. Although shown as being between mid-section 6 and front section 7, the expanded core section of portion 44 may also be located elsewhere along the shaft provided that it is distal to neck section 5. Also, it will be understood that an expanded core section of the type described above is not limited to bone screw 1 shown in FIG. 12, but may also find application in other screws disclosed herein, including, bone screw 1 of FIGS. 1 and 7. Finally, although the expanded core section of portion 44 may have a major diameter that is larger than the major diameter of either front section 7 or mid-section 6 (as shown in FIG. 2), an expanded core section of portion 44 where the major diameter is equal to the remainder of the screw diameter will provide a screw of a uniform major diameter and may be preferred.

Set forth in Tables 3 and 4 are additional listings of certain exemplary bone screws like bone screw 1 of FIG. 12 with, among other things, the relative lengths of neck section 5, mid-section 6 and front section 7 for a bone screw having a selected major diameter ($d_{maj}$). The listings provided below are not intended to be exhaustive or limit the scope of the invention in any way. Thus, bone screws listed in Table 3 are typically made of stainless steel and have a mid-section 6 with a major diameter of between approximately 3.35 mm-3.5 mm, a mid-section minor diameter of between approximately 2.45 mm-2.60 mm; a front section 7 minor diameter of between approximately 2.59 mm-2.74 mm and a major diameter of between approximately 3.35 mm-3.5 mm, and a neck section 5 diameter of between approximately 2.55 mm-2.65 mm. In addition, screws listed in Table 3 will typically have an expanded core portion 44 with a major diameter of between approximately 3.4 mm-3.5 mm, a minor diameter of between approximately 3.15 mm-3.25 mm, and a thread height of between 0.05-0.175. The expanded core portion preferably expands the original diameter of pilot hole 15 original diameter (approximately 2.667 mm-2.718 mm) to provide neck section 5 with a clearance of approximately 0.25 mm-0.35 mm on each side.

TABLE 3

| $d_{maj}$/Length (mm) | Neck Section (mm) | Mid-Section (mm) | Front Section (mm) | Expanded Core (mm) |
|---|---|---|---|---|
| 3.5/24 | 7.5 | 3 | 8 | 2 |
| 3.5/26 | 8.5 | 5 | 8 | 2 |
| 3.5/28 | 9.5 | 7 | 8 | 2 |
| 3.5/30 | 9.5 | 7 | 10 | 2 |
| 3.5/32 | 9.5 | 9 | 10 | 2 |
| 3.5/34 | 10.5 | 11 | 10 | 2 |
| 3.5/36 | 11.5 | 13 | 10 | 2 |
| 3.5/38 | 12.5 | 15 | 12 | 2 |
| 3.5/40 | 12.5 | 17 | 12 | 2 |
| 3.5/42 | 12.5 | 19 | 12 | 2 |
| 3.5/44 | 12.5 | 21 | 12 | 2 |
| 3.5/46 | 12.5 | 23 | 12 | 2 |
| 3.5/48 | 12.5 | 21 | 12 | 2 |
| 3.5/50 | 12.5 | 23 | 12 | 2 |
| 3.5/52 | 12.5 | 25 | 12 | 2 |
| 3.5/54 | 12.5 | 27 | 12 | 2 |
| 3.5/56 | 12.5 | 29 | 12 | 2 |
| 3.5/58 | 12.5 | 31 | 12 | 2 |
| 3.5/60 | 12.5 | 33 | 12 | 2 |

Bone screws listed in Table 4 may likewise typically be made of stainless steel and may have a mid-section major diameter of approximately 4.35 mm-4.5 mm and a minor diameter of between approximately 3.05 mm-3.2 mm, a neck section diameter of between approximately 3.35 mm-3.45 mm, a front section major diameter of between approximately 4.35 mm-4.5 mm and minor diameter of between approximately 3.28 mm-3.43 mm. The bone screws listed in Table 4 may have an expanded core portion 44 with a major diameter of between approximately 4.4 mm-4.5 mm, a minor diameter of between approximately 4.18 mm-4.28 mm with a thread height of between approximately 0.035 mm-0.16 mm. Expanded core portion 44 expands pilot hole 15 (from an approximate original diameter 3.66 mm-3.71 mm) to provide a gap of between approximately 0.365 mm-0.465 mm on either side of neck section 15.

TABLE 4

| $d_{maj}$/Length (mm) | Neck Section (mm) | Mid-Section (mm) | Front Section (mm) | Expanded Core (mm) |
|---|---|---|---|---|
| 4.5/24 | 7.5 | 5 | 8 | 2 |
| 4.5/26 | 8.5 | 7 | 8 | 2 |
| 4.5/28 | 9.5 | 7 | 8 | 2 |
| 4.5/30 | 9.5 | 7 | 10 | 2 |
| 4.5/32 | 9.5 | 9 | 10 | 2 |
| 4.5/34 | 10.5 | 11 | 10 | 2 |
| 4.5/36 | 11.5 | 11 | 10 | 2 |
| 4.5/38 | 12.5 | 11 | 12 | 2 |
| 4.5/40 | 12.5 | 13 | 12 | 2 |
| 4.5/42 | 12.5 | 15 | 12 | 2 |
| 4.5/44 | 12.5 | 17 | 12 | 2 |
| 4.5/46 | 12.5 | 19 | 12 | 2 |
| 4.5/48 | 12.5 | 21 | 12 | 2 |
| 4.5/50 | 12.5 | 23 | 12 | 2 |
| 4.5/52 | 12.5 | 25 | 12 | 2 |
| 4.5/54 | 12.5 | 27 | 12 | 2 |
| 4.5/56 | 12.5 | 29 | 12 | 2 |
| 4.5/58 | 12.5 | 31 | 12 | 2 |
| 4.5/60 | 12.5 | 33 | 12 | 2 |

Figure 13:
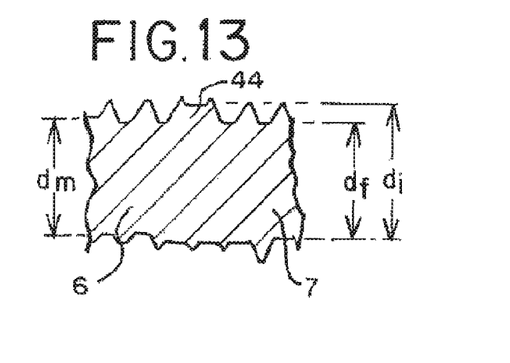
FIG. 13 is a cross-sectional view of a portion of the bone screw of FIG. 12 taken along line 13-13 and showing an expanded core section.
Figure 14:
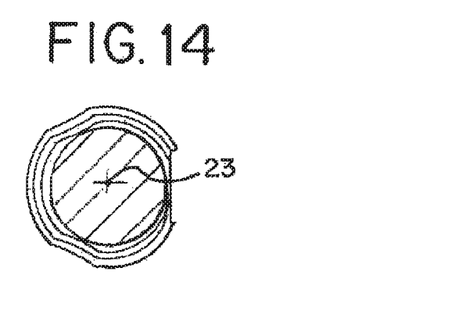
FIG. 14 is a cross-sectional end view of the bone screw of FIG. 12 taken along lines 14-14.
Figure 15:
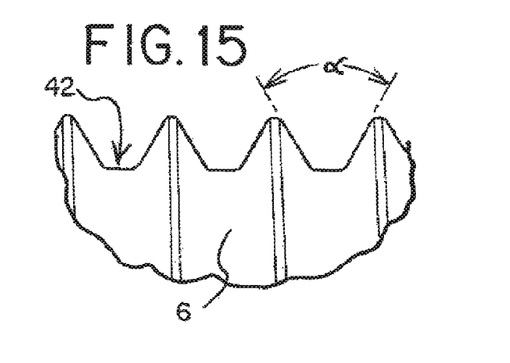
FIG. 15 is an enlarged side view of the thread profile of the mid-section of the bone screw of FIG. 12.
Figure 16:
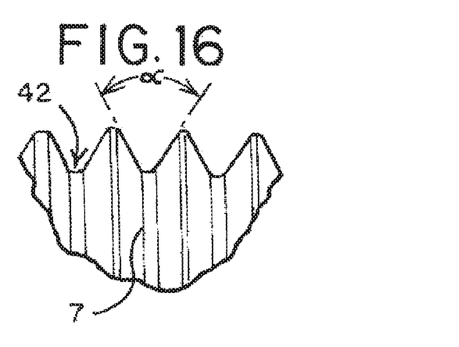
FIG. 16 is an enlarged side view of the thread profile of the front section of the bone screw of FIG. 12.

With regard to thread pitch, mid-section 6 and front section 7 may have an identical pitch as shown in FIG. 13 or may have a different pitch as described above in connection with the embodiment of FIG. 7. Finally, other differences in thread profile between mid-section 6 and front section 7 may include the shape of the thread root 42. As shown in FIGS. 15-16, thread root 42 of the threaded front section 7 includes a flattened portion at the root in contrast to the shorter flattened portion of the thread root in the threaded portion of mid-section 6 shown in FIG. 16. The shallower thread root of front section 7 may also be more torroidal rather than defined by discrete angles.

In addition, the screws shown in FIGS. 12-16 may also include a threaded head, as previously shown and described. Threaded head engages the corresponding threads found in apertures 14 and eliminates the need for a locking cap described below and shown in FIGS. 5, 17-18.

In accordance with the surgical method of forming a bone construct for bone healing, bone plate 2 is provided and placed against bone 3 as seen in FIG. 5. As indicated above, plate 2 is anatomically contoured to substantially conform to the shape of the bone undergoing treatment whether it is the femur, tibia or humerus, or other bone. Spacers may be provided to lift plate 2 off the bone during attachment. Typically, several bone screws are used and are introduced through the apertures 14 of plate 2. The type and size of screws is selected by the surgeon after X-ray or other analysis of the patient's bone features, and measurement (by depth gauge, for example) of the pre-drilled hole. Verification of correct screw insertion (e.g., such that the threads of the bone screw 1 mid-section 6 are not engaged in near cortex 12) may be achieved by fluoroscopy or other diagnostic means.

Where bone plate 2 requires attachment to the metaphysis or epiphysis of bone 3, one or more screws 50 (FIG. 5) adapted for engaging cancellous bone, as previously described, may be introduced by the surgeon through apertures at one or both of the ends 34, 36 of bone plate 2. Bone screws 1 of the type described herein and particularly the bone screw 1 like those shown in FIGS. 7-18 are preferably used to attach plate 2 along the diaphysis of bone 3. Placement of different types of bone screws (i.e., cancellous, bi-cortical locking, far cortical locking) will depend, in part, on the number and location of the fracture(s). For example, for a single fracture site 31' (shown in broken lines in FIG. 5) cancellous screws 50 may be inserted at the metaphysis 52 of bone 3. Bi-cortical locking bone screws (not shown) may also be used for cortical engagement in the bone segment that includes the metaphysis 52. Bone screws 1 of the type disclosed herein and shown, for example, in FIGS. 7-18 are preferable inserted at the diaphysis 54 on the other side of fracture site 31'. Alternatively, for a single fracture site 31, plate 2 is placed along the diaphysis entirely and thus bridges fracture site 31 as shown in FIG. 6. In this example, bone screws 1 of the type shown in FIGS. 7-18 may be placed on both sides of fracture site 31 as also shown in FIG. 6. Typically, an equal number of the bone screws 1 will be placed on either side of fracture site 31. In a further example, where multiple fracture sites (e.g., 31 and 31') exist, all of the bone screws in the segments of the diaphysis 54 may be bone screws 1 of the present disclosure as shown in FIG. 5.

Figure 17:
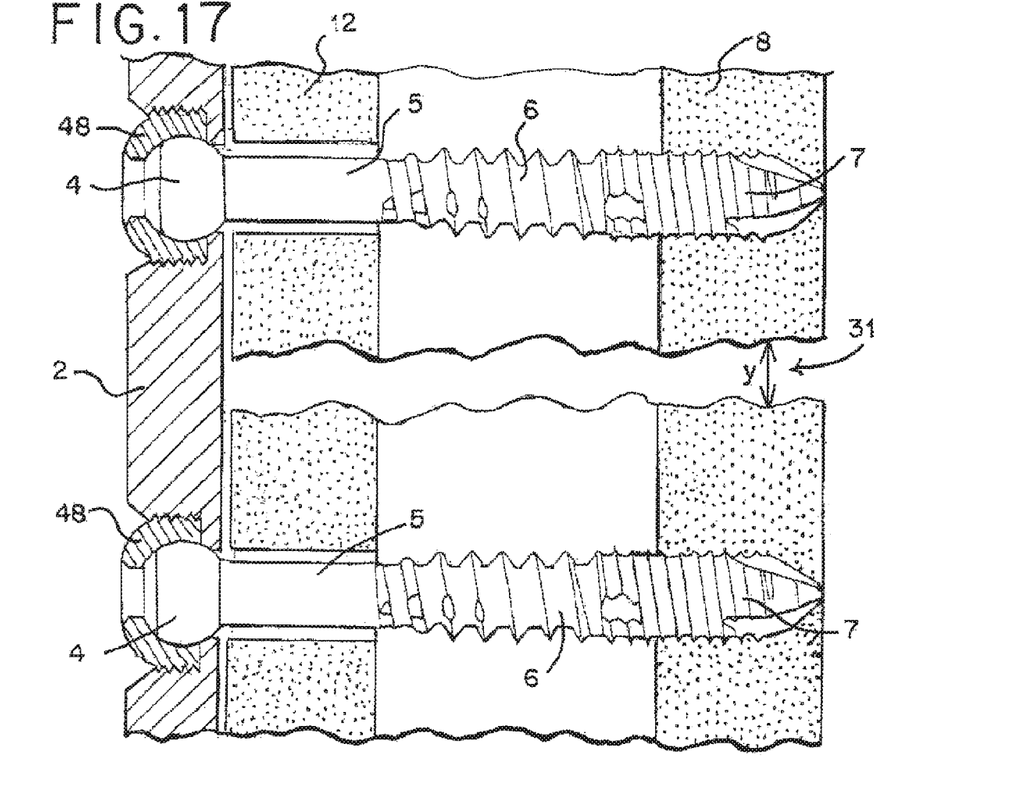
FIG. 17 is an enlarged view of a portion of the fracture site of FIG. 6.

Prior to inserting bone screws 1, a pilot hole is provided using a dedicated drill, as will be known and recognized by those of skill in the art. In the case of bone screw 1, the pilot hole should be of a diameter sufficient to accommodate the major diameter of bone screw 1. In addition, pilot hole 15 should have a diameter sufficient to provide a gap on either side of neck section 5, as shown in FIG. 17, to allow for limited movement of neck section 5 within pilot hole 15 of the near cortex 12. As noted above, it is desired that a gap of between 0.2-0.6 mm and, more preferably, about 0.5 mm be provided on either side of neck section 5 in the near cortex 12 of bone 3. A gap such as this allows for the limited movement of bone screw 1. Such movement of neck section 5 and, indeed, neck section 5 and mid-section 6 translates into comparable and substantially uniform degrees of motion at both the near and far cortex 12, 8, respectively, (depending on, of course, the screw size) and is substantially within the 0.2-1.0 mm stimulation range at fracture site 31 or 31' that is believed to promote callus formation.

Once pilot hole 15 has been drilled, the desirable bone screw 1 is selected. Bone screw 1 is selected based on the previously diagnosed characteristics of the patient's bone. For example, a bone screw that when fully inserted has a front section 7 that can fully engage far cortex 8, a mid-section that does not in any significant way engage any part of the bone during far cortical engagement by front section 7, and a neck section that resides substantially within pilot hole 15, as shown in FIG. 17 is preferred. Selected bone screw 1 is then introduced through aperture 14 of plate 2 and advanced into bone 3. As bone screw is further advanced and front section 7 contacts bone in the far cortex 8, the dual lead thread having a finer pitch of front section 7 advances through the dense cortical bone. As shown in FIG. 6, front section 7 of bone screw 1 advances into the cortical bone of the far cortex 8, such that substantially the entire front section 7 resides in the far cortical bone. Similarly, no part of threaded mid-section 6 resides or contacts any portion of the cortical bone, whether at he near or far cortex 12, 8, respectively.

Figure 18:
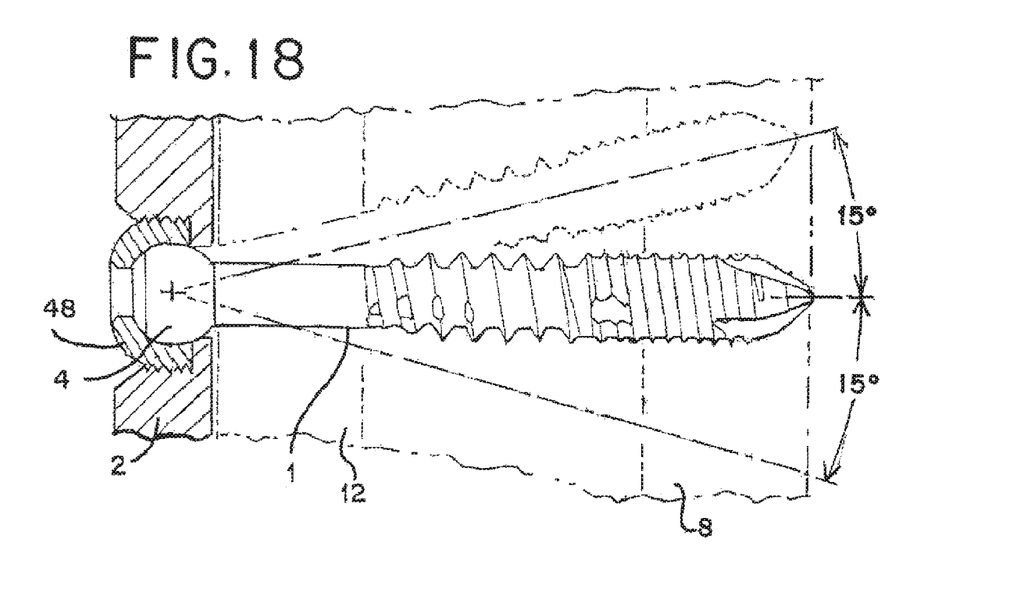
FIG. 18 is an enlarged view of a bone screw of the present disclosure, including a bone screw cap, wherein the bone screw is inserted at an angle to the central axis of the plate aperture.

If head portion 4 is unthreaded and itself does not engage the portion of bone 3 defining the aperture 15, threaded cap 48 may be provided over head portion 4, as shown in FIG. 5 and FIGS. 17-18. Threaded cap 48 defines an inner shell that receives the typically spherical head of bone screw 1 and accommodates head portion 4 of a screw that has been inserted in something other than perpendicular fashion to bone plate 2, as shown in FIG. 18. The angle of bone screw insertion may be offset from the central axis of aperture 14 by approximately 15° or less as also shown in FIG. 18. While insertion of bone screw 1 at some angle to the central axis of aperture 14 is possible, with bone screws 1 of the present disclosure and, in particular, the embodiments of FIGS. 5-18, substantially perpendicular insertion of bone screw 1 is more typical and may be preferred. Alternatively, if head portion 4 is threaded, as shown, for example, in FIG. 12, it will engage the internal threads of plate aperture 14 directly. In some embodiments, it may be desirable to further include bone spacers between plate 2 and the surface of bone 3, such as those described in co-pending U.S. Patent Application Publication No. 2007/0191848, the entire disclosure of which is expressly incorporated herein.

Study

A study was conducted to establish a stiffness profile and to demonstrate micromotion of the near and far cortices relative to the plate. Bone screws 1 of the type described herein and shown, more particularly, in FIG. 7, were used in constructs applied to simulated bone. The results were compared to identical constructs using only bi-cortical locking screws. Used in the Study were far cortical locking bone screws 1, made by Zimmer, Inc. of Warsaw, Ind., having a diameter of 4.0 mm and a length 32 mm and identified by Zimmer part number 02.03162.032 and a tibial plate, also available form Zimmer, Inc., of Warsaw, Ind., identified by Zimmer part number 02.02261.309. Bi-cortical locking screws for the tibial construct testing were also used. The bi-cortical locking screws likewise had a diameter (major) of 4.0 mm and a length of 32 mm and are available from Zimmer, Inc., and identified by the part number 02.03155.032.

In the femoral construct study, bone screws of the type described herein having a diameter of 5.0 mm and a length of 38 mm available from Zimmer, Inc., of Warsaw, Ind. under part number 02.03161.038 were used with a femoral plate, also available from Zimmer, Inc. and identified by Zimmer part number 02.03260.113. Bi-cortical locking screws for the femoral construct testing were also used. These screws likewise had a diameter (major) of 5.0 mm and a length of 38 mm and are available from Zimmer. Inc., of Warsaw, Ind., under the product number 02.03150.038. The constructs and testing methods used in the study are summarized below:

Implants were evaluated in test constructs representing an unstable fracture of the femoral diaphysis being bridged by a plating construct. The femoral diaphysis was simulated by $4^{th}$ generation synthetic cylinders (Sawbones Worldwide, Pacific Research Laboratories, Inc., P/N #3403-10) of 27 mm outer diameter, 7 mm wall thickness, and 500 mm length. The tibial diaphysis was likewise simulated by $4^{th}$ generation synthetic cylinders (Sawbones, P/N #3403-21). Plates were applied with four consecutive screws proximal and with four consecutive screws distal to a 10 mm parallel fracture gap, with the central screw hole of the plate segment being located over the fracture gap. Plates were applied a 2 mm elevation using blue bone spacers, which are most commonly used clinically-when spacers are used. In the far cortical locking group, the four proximal screws were far cortical locking screws, as identified above, and the remaining screws were bi-cortical screws, likewise identified above. In the bi-cortical locking control group, all eight screws were bi-cortical locking screws of the type described above.

For assembly of the constructs using the plate alignment fixture, the pre-cut sawbones were placed into both sides of the fixture and held in place. The 2 mm spacers were inserted into two holes of the plate, one on each side of the osteotomy gap. The fifth hole of the plate was placed over the dowel pin in the alignment fixture and the side alignment guide was attached.

All screws were inserted after bi-cortical pre-drilling with the appropriate diameter drill bit. All holes were pre-drilled, except for those with the spacers located in them. The holes were drilled substantially parallel to the osteotomy. The appropriate screws ere inserted, in accordance with the construct. All screws were fixed to the plate with locking screw caps tightened to 6 Nm. The spacers were removed and the remaining holes were drilled. The screw placement was completed for the appropriate configuration.

Test constructs were loaded in axial compression via loading fixtures, designed to replicate a loading mode that generally resembles physiologic loading of the human femur and tibia, respectively. Both fixtures were made of Delrin and were intended to replicate the average stiffness of the femur or tibia. This allows for applying the determined proximal joint reaction force loads at their respective orientation.

Figure 19:
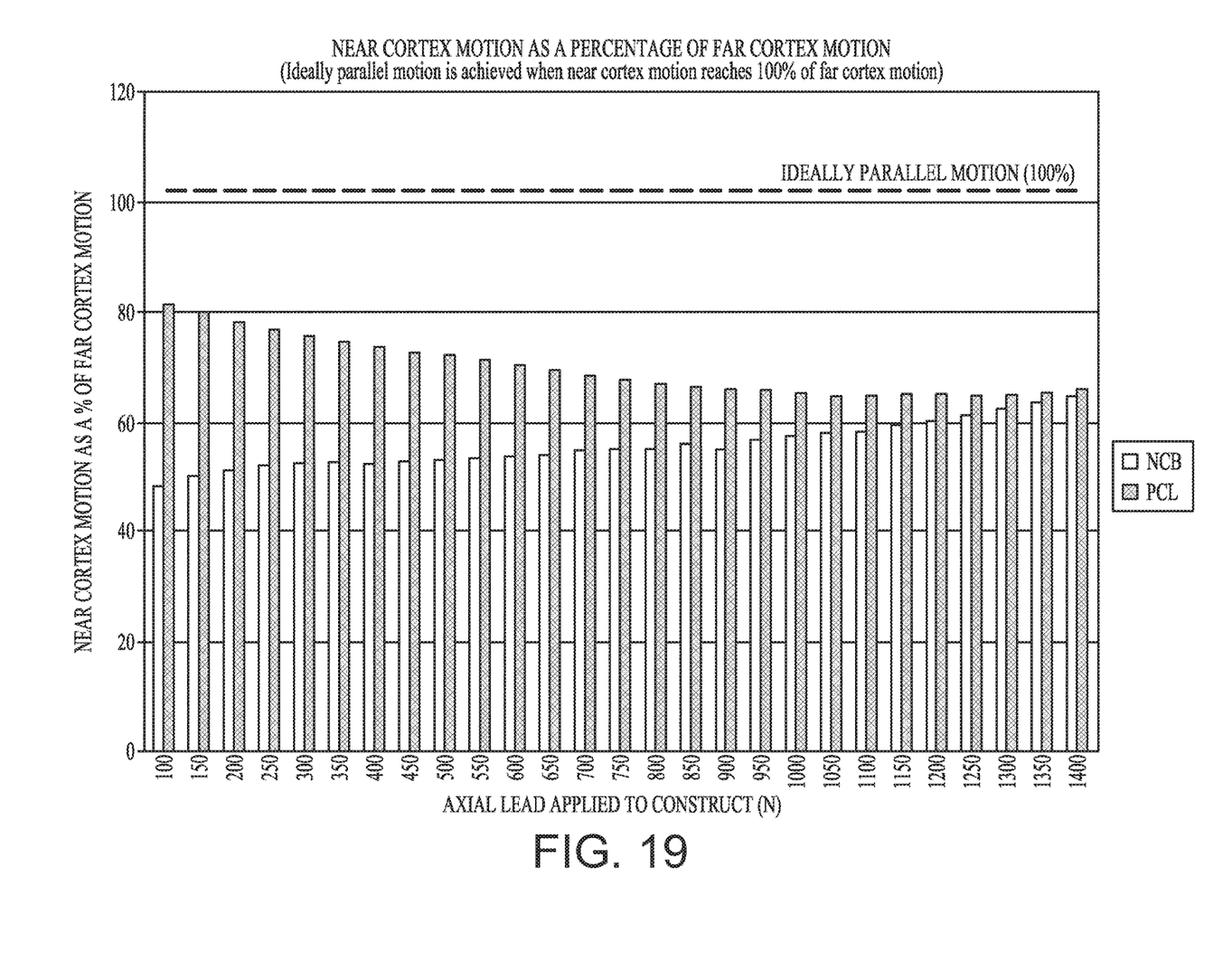
FIG. 19 is a graph showing near cortex motion as a percentage of far cortex motion in a simulated tibial diaphysis with constructs using bone screws of the present disclosure and constructs using only bi-cortical locking screws.
Figure 20:
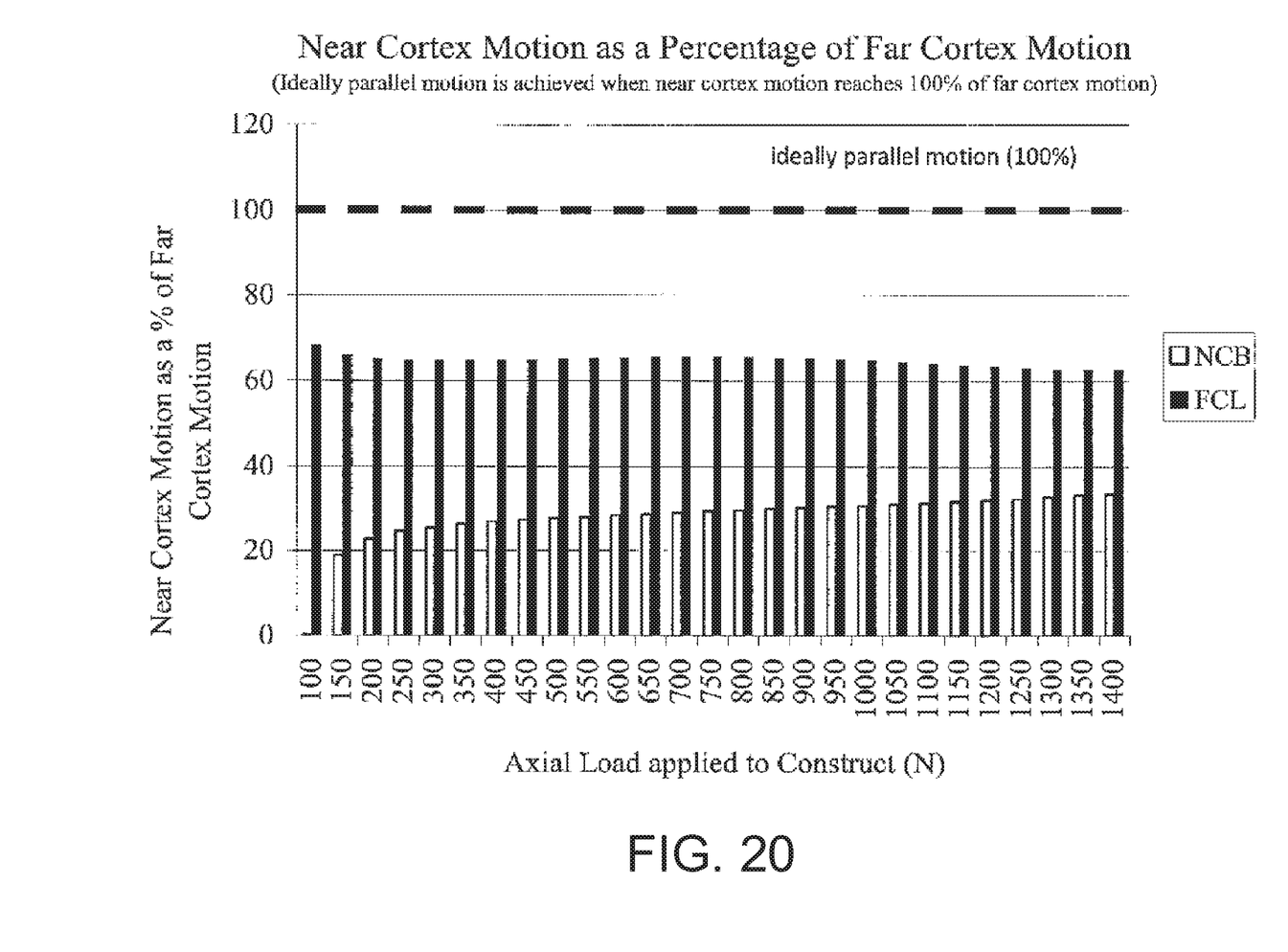
FIG. 20 is a graph showing near cortex motion as a percentage of far cortex motion in a simulated femoral diaphysis with constructs using bone screws of the present disclosure and constructs using only bi-cortical locking screws.

Motion at both the near and far cortex was measured in both the femoral and tibial studies. The percent motion of the cortices was normalized to near cortex using the following calculation:

$$\frac{\text{Near Cortex Displacement}}{\text{Far Cortex Displacement}} \times 100\%$$

The value is the percent relative motion of the near cortex to the far cortex. FIGS. 19 and 20 show the results of the study for the tibial and femoral constructs. respectively. As shown in FIGS. 19 and 20, the ratio of motion at the near and far cortices for both femoral and tibial constructs was greater than approximately 50%, greater than approximately 60% and in some instances greater than approximately 80% within an initial stiffness range of less than 600N axial loading, using cortical locking bone screws of the type disclosed herein. In contrast, constructs using only the bi-cortical locking screws allowed for motion at the near end far cortex that was less parallel by approximately 40-60% for the femur and approximately 30-35% for the tibia at comparable loading conditions.

In addition to providing a construct that has an overall stiffness that is reduced when compared to other constructs that use bi-cortical locking screws, bone screws 1 of the present disclosure likewise provide sufficient strength under expected load conditions.

Thus, it can be seen from the foregoing description, bone screw 1, osteosynthesis construct formed used bone screw 1, and methods for using them, may provide one or more of the following advantages:

Far cortex fixation provides a less stiff, more flexible osteosynthesis construct as compared to alternative plate and screw osteosynthesis constructs.

Less stiff far cortex fixation can reduce stress concentrations in bone, which in turn can reduce the incident of bone fractures caused by the osteosynthesis construct, especially in case of osteoporotic bone.

The stiffness of the fixation construct can be adjusted by varying the number of far cortex fixation screws that connect the plate to a bone segment by means of a positive-locking mechanism.

Provision of a controlled failure mechanism by screw shaft bending to delay or prevent more detrimental failure modes, such as plate bending or bone fracture.

The flexible screw shaft improves the ability to engage the threaded screw head with the plate hole thread, especially when the screw holes in the bone and plate are not precisely concentric.

Provision of a means for fracture site compression by means of non-concentric insertion of the screw in the far cortex, so that the screw head can only engage in the plate hole thread if a force perpendicular to the screw central axis is applied to the screw head.

Although specific embodiments have been illustrated and described herein, it will be appreciated by those of ordinary skill in the art that a wide variety of alternate and/or equivalent implementations may be substituted for the specific embodiments shown and described, without departing from the scope of the present invention. This application is intended to cover any adaptations or variations of the embodiments discussed herein. Therefore, it is manifestly intended that this invention be limited only by the claims and the equivalents thereof.

What is claimed is:

1. A bone screw, comprising:
   a) a head portion; and
   b) a shaft portion, including:
      an unthreaded proximal neck section,
      a threaded mid-section; and
      a threaded front section distal to said mid-section,
   wherein the threaded mid-section has a first thread profile different from a second thread profile of the threaded front section and the threaded front section is configured for engaging cortical bone,
   wherein the threaded mid-section has a first maximum core diameter, along the first thread profile, that is less than a second maximum core diameter, along the second thread profile, of the threaded front section, and
   wherein a maximum diameter of the unthreaded neck section and the first maximum core diameter of the threaded mid-section are less than the second maximum core diameter of said front section.

2. The bone screw of claim 1, wherein the shaft portion further includes an expanded core section having a third maximum core diameter that is greater than the first maximum core diameter of the threaded mid-section and the second maximum core diameter of the threaded front section.

3. The bone screw of claim 2, wherein a first major diameter of the expanded core section is equal to a second major diameter of the threaded mid-section and a third major diameter of the threaded front section.

4. The bone screw of claim 2, wherein the expanded core section is positioned distal to the unthreaded neck section.

5. The bone screw of claim 2, wherein the expanded core section is positioned between the threaded mid-section and the threaded front section.

6. The bone screw of claim 2, wherein the expanded core section includes a cutting element.

7. The bone screw of claim 2, wherein the third maximum core diameter of the expanded core section is larger than a maximum diameter of the unthreaded neck section by a pre-determined amount.

8. The bone screw of claim 1, wherein the diameter of the unthreaded neck section is substantially equal to the first maximum core diameter of the threaded mid-section.

9. The bone screw of claim 1, wherein the threaded mid-section has a first pitch that is greater than a second pitch of the threaded front section.

10. The bone screw of claim 1, wherein the threaded mid-section includes a reverse thread.

11. The bone screw of claim 1, wherein the threaded mid-section includes a plurality of cutting flutes spaced about a central axis of the bone screw.

12. The bone screw of claim 1, wherein the first thread profile includes a first thread angle and a first root shape and the second thread profile includes a second thread angle and a second root shape, wherein the first thread angle and the second thread angle are the same and the first root shape is different from the second root shape.

13. The bone screw of claim 1, wherein the first thread profile includes a first thread that extends helically, at least once, around the entire circumference of the threaded mid-section, and wherein the second thread profile includes a second thread that extends helically, at least once, around the entire circumference of the threaded front section.

14. The bone screw of claim 1, wherein the threaded front section has a first major diameter that is equal to a second major diameter of the threaded mid-section.

15. A bone screw, comprising:
a) a head portion; and
b) a shaft portion, including:
  a proximal unthreaded neck section,
  a threaded mid-section; and
  a threaded front section distal to said mid-section, the proximal unthreaded neck section extending from the head portion to the threaded mid-section;
wherein the threaded mid-section has a first thread profile having a first pitch and the threaded front section has a second thread profile having a second pitch, wherein the first pitch is greater than the second pitch,
wherein a maximum diameter of the proximal unthreaded neck section is constant and equal to a first maximum core diameter of the threaded mid-section, and
wherein the maximum diameter of the unthreaded neck section and the first maximum core diameter of the threaded mid-section are less than a second maximum core diameter of the threaded front section.

16. The bone screw of claim 15, wherein the first thread profile has a reverse thread.

17. The bone screw of claim 16, wherein threaded mid-section includes a plurality of cutting flutes spaced about a central axis of the bone screw.

18. A bone screw, comprising:
a) a head portion; and
b) a shaft portion, including:
  an unthreaded proximal neck section,
  a threaded mid-section; and
  a threaded front section distal to said mid-section,
wherein the threaded mid-section has a first thread profile different from a second thread profile of the threaded front section and the threaded front section is configured for engaging cortical bone, wherein the unthreaded proximal neck section extends from the head portion to the first thread profile of the threaded mid-section, the threaded mid-section extending from the unthreaded proximal neck section to the second thread profile of the threaded front section,
wherein the first thread profile has a first maximum length that is greater than a second maximum length of the second thread profile,
wherein a third maximum length of the unthreaded proximal neck section is at least half of the second maximum length of the second thread profile, and
wherein the first thread profile includes a first thread angle and a first root shape and the second thread profile includes a second thread angle and a second root shape, wherein the first thread angle and the second thread angle are the same and the first root shape is different from the second root shape.

19. The bone screw of claim 18, wherein the first thread profile has a reverse thread.

* * * * *